United States Patent
Enomura et al.

(10) Patent No.: US 10,676,418 B2
(45) Date of Patent: Jun. 9, 2020

(54) METHOD FOR PRODUCING MICROPARTICLES FROM PRESSURIZED AND HEATED STARTING MATERIAL SOLUTION

(71) Applicant: M. TECHNIQUE CO., LTD., Izumi-shi, Osaka (JP)

(72) Inventors: Masakazu Enomura, Izumi (JP); Kaeko Araki, Izumi (JP)

(73) Assignee: M. TECHNIQUE CO., LTD., Izumi-Shi (JP)

( * ) Notice: Subject to any disclaimer, the term of this patent is extended or adjusted under 35 U.S.C. 154(b) by 0 days.

(21) Appl. No.: 16/330,202

(22) PCT Filed: Sep. 5, 2017

(86) PCT No.: PCT/JP2017/031962
§ 371 (c)(1),
(2) Date: Mar. 4, 2019

(87) PCT Pub. No.: WO2018/043755
PCT Pub. Date: Mar. 8, 2018

(65) Prior Publication Data
US 2019/0202765 A1    Jul. 4, 2019

(30) Foreign Application Priority Data
Sep. 5, 2016 (JP) ................. 2016-173038

(51) Int. Cl.
C07C 45/81 (2006.01)
C07J 53/00 (2006.01)
C09B 61/00 (2006.01)
B01D 9/00 (2006.01)

(52) U.S. Cl.
CPC ............ *C07C 45/81* (2013.01); *B01D 9/0054* (2013.01); *C07J 53/004* (2013.01); *C09B 61/00* (2013.01); *B01D 2009/0095* (2013.01)

(58) Field of Classification Search
CPC ...... C07C 45/81; C07J 53/004; B01D 9/0054; B01D 2009/0095; C09B 61/00
See application file for complete search history.

(56) References Cited

U.S. PATENT DOCUMENTS

| 6,048,560 A | 4/2000 | van Dort et al. |
| 2006/0024242 A1* | 2/2006 | Oshiro ............ A61K 9/08 424/46 |
| 2010/0155310 A1 | 6/2010 | Enomura |
| 2011/0190399 A1 | 8/2011 | Kar et al. |
| 2014/0161915 A1* | 6/2014 | Payne ............ A61K 31/12 424/756 |

FOREIGN PATENT DOCUMENTS

| EP | 2184109 A1 | 5/2010 |
| JP | 53-130412 | 11/1978 |
| JP | 10-512614 A | 12/1998 |
| JP | 2005-328839 A | 12/2005 |
| JP | 2009-263638 A | 11/2009 |
| JP | 2011-189348 A | 9/2011 |
| JP | 2011-250708 A | 12/2011 |
| WO | WO 96/22702 A1 | 8/1996 |
| WO | WO 2010/013224 A2 | 2/2010 |
| WO | WO 2013/078477 A2 | 5/2013 |

OTHER PUBLICATIONS

Pressurize, Merriam-Webster, Recovered from https://www.merriam-webster.com/dictionary/pressurize on Apr. 29, 2019, pp. 1-10. (Year: 2019).*
International Search Report, issued in PCT/JP2017/031962, dated Oct. 10, 2017.
Extended European Search Report, dated Mar. 16, 2020 for European Application No. 17846758.5.
Kim et al., "Optimization, in vitro release and bioavailability of γ-oryzanol-loaded calcium pectinate microparticles reinforced with chitosan", New Biotechnology, Sep. 2010, vol. 27, No. 4, pp. 368-373 (6 pages).

* cited by examiner

*Primary Examiner* — Paul A Zucker
(74) *Attorney, Agent, or Firm* — Birch, Stewart, Kolasch & Birch, LLP

(57) ABSTRACT

The present invention addresses the problem of providing a method for efficiently producing uniform microparticles of curcumin and/or γ-oryzanol at a higher yield. The target microparticles are produced by dissolving a starting material in a solvent to give a starting material solution and then subjecting the starting material solution to crystallization by a poor solvent method to thereby deposit the starting material. To prepare the starting material solution, curcumin and/or γ-oryzanol are used as the starting material(s) and ethanol is used as the solvent. The starting material(s) and the solvent are stirred in a pressurized state at a temperature of 78.3-130° C. inclusive to give the starting material solution. Then, the starting material solution thus obtained is subjected to crystallization by the poor solvent method and thus the target microparticles are produced.

7 Claims, 3 Drawing Sheets

METHOD FOR PRODUCING MICROPARTICLES FROM PRESSURIZED AND HEATED STARTING MATERIAL SOLUTION

TECHNICAL FIELD

The present invention relates to a method for producing microparticles from a pressurized and heated raw material solution, especially to a method for producing curcumin microparticles or γ-oryzanol microparticles.

BACKGROUND ART

Curcumin, which is a yellow pigment of ukon or turmeric (scientific name; *Curcuma longa*) which is a spice component of curry, is classified as curcuminoid, a kind of polyphenol. Therefore, curcumin is known as an antioxidant so that it is used not only as a natural pigment but also in health drinks and health foods having an improvement action of a lever function. Curcumin is also known to have an antitumor action, an antioxidant action, an anti-immune action, and the like; and thus, it is expected to be widely utilized in a medical drug. On the other hand, γ-oryzanol is a compound included in rice bran and so forth, and whereby it has many health effects such as reduction of blood lipids, growth facilitation, and easing of a menopause symptom, so that it is utilized in a medical drug, besides foods and cosmetics.

Both curcumin and γ-oryzanol are substances hardly soluble in water so that improvement in an absorption property thereof into a living body is required. In order to solve this problem, it is presumed that micronization of these substances to the size of less than several micrometers is effective (Patent Document 1).

With regard to the micronization method of curcumin, as described in Patent Document 2, a method is known in which after the turmeric pigment is added into a ghatti gum-including aqueous solution, the turmeric pigment is subjected to the crushing treatment until the average particle diameter thereof reaches 1 μm or less. However, the treatment time thereof is very long; and in addition, because a media mill such as a bead mill is generally used in the crushing treatment, there remains a problem of generating foreign materials derived from the media, so that the improvement thereof is required.

In the method in which curcumin is crushed by using a mechanical crusher such as a homogenizer, not only uniform micronization of curcumin is difficult but also there is a problem in durable stability. In order to solve these problems, in Patent Document 3, a method is described in which an ethanol solution having curcumin dissolved therein is mixed with and dispersed into a raw material water so as to micronize curcumin thereby obtaining a dispersion solution of finely crushed curcumin with the size of 200 nm or less. Specifically, in Example 3 of Patent Document 3, as the ethanol solution having curcumin dissolved therein, an ethanol solution having 0.5 g of 98% curcumin dissolved into 100 mL of 95% ethanol is prepared. In this Example 3, the temperature condition at the time of preparation of the ethanol solution is not described; however, because solubility of curcumin in ethanol is about 0.5% by weight (25° C.), curcumin is micronized by using the almost saturated ethanol solution thereof. However, because the curcumin concentration in the ethanol solution is too dilute, many problems are pointed out such as the waste water treatment and removal of ethanol in the subsequent processes, as well as the large processing facility. These backgrounds are also the same in γ-oryzanol (Patent Document 4). Accordingly, methods for efficiently producing microparticles with low industrial cost are required in both curcumin and γ-oryzanol.

CITATION LIST

Patent Documents

Patent Document 1: Japanese Patent Laid-Open Publication No. 2011-250708
Patent Document 2: Japanese Patent Laid-Open Publication No. 2009-263638
Patent Document 3: Japanese Patent Laid-Open Publication No. 2005-328839
Patent Document 4: Japanese Patent Laid-Open Publication No. S53-130412

DISCLOSURE OF INVENTION

Problems to be Solved by the Invention

In the methods for producing the curcumin microparticles or the γ-oryzanol microparticles wherein curcumin or γ-oryzanol is micronized so as to obtain the curcumin microparticles or the γ-oryzanol microparticles, there have been the following problems.
1) In the crushing method using a mechanical crusher such as a homogenizer, along treatment time is required, and a durable stability cannot be ensured.
2) In the crushing method using media such as a bead mill, contamination of foreign materials derived from the media can take place.
3) In the method wherein a solution having curcumin or γ-oryzanol dissolved in a solvent capable of becoming a good solvent to curcumin or γ-oryzanol is mixed with a solvent (poor solvent) having lower solubility to curcumin or γ-oryzanol than the above-mentioned solution thereby separating the curcumin microparticles or the γ-oryzanol microparticles, i.e., in a so-called poor solvent method, because of the solubility problem of curcumin or γ-oryzanol in the above-mentioned solvent, only a dilute solution can be prepared, and therefore, this method causes increase in the waste water as well as a high cost in the production thereof.
4) Alternatively, among others there is also a method wherein microparticles are obtained by melting curcumin or γ-oryzanol together with a polymer or the like; however, in this method, the temperature needs to be raised to at least 183° C., which is a melting point of curcumin, or to at least 137° C., which is a melting point of γ-oryzanol. Therefore, under these temperatures, there is a risk of denaturing or decomposition of curcumin, γ-oryzanol, or the polymer.

The present invention intends, in the method for producing curcumin microparticles or γ-oryzanol microparticles wherein a raw material solution is prepared by dissolving curcumin or γ-oryzanol, which are raw materials of these microparticles, into ethanol followed by a crystallization operation of the raw material solution by means of a poor solvent method, to provide a method for efficiently and uniformly producing these microparticles in a higher yield.

The inventor of the present invention found that solubilities of these raw materials to ethanol are increased by dissolving these raw materials into ethanol under a heated and pressurized state by using an airtight vessel at the time when these raw materials are dissolved into ethanol. Namely, these materials could be dissolved into ethanol even with the concentration thereof being more than 5% by weight under the pressurized and heated state with the temperature of not lower than 78.3° C., which is a standard boiling point (boiling point at the pressure of 1 atm) of ethanol. This is a surprising phenomenon in view of the fact that these raw materials can be dissolved into ethanol with the amount of only about 0.5% by weight under normal temperature and pressure. More surprisingly, it was found that in the ethanol solutions of these raw materials that were obtained by dissolving them once under the pressurized state in the temperature range of 78.3° C. or higher and 130° C. or lower, precipitation of the raw materials therefrom was more difficult even when the temperatures thereof were lowered after the dissolution as compared with the ethanol solutions of the raw materials which were obtained by dissolving them under normal temperature and pressure. In other words, it was found that highly soluble raw material solutions could be obtained by preparing the raw material solutions under the conditions as mentioned above.

It was found that the highly soluble raw material solution could be retained above a certain temperature determined by concentration of the raw material in the ethanol solution so that the solution could be stably used even below 78.3° C., which is the standard boiling point of ethanol. On the basis of this finding, the present invention could be completed.

Means for Solving the Problems

In the method for producing microparticles of the above-mentioned raw material wherein the raw material solution having the raw material dissolved in a solvent is prepared, which is then followed by carrying out a precipitation operation by means of a poor solvent method using the raw material solution thus prepared so as to obtain the microparticles of the raw material, the present invention solves the above-mentioned problems by preparing the raw material solution by the way as described below.

In the present invention, at the time when the raw material solution is prepared, at least any one of curcumin and γ-oryzanol is used as the raw material, and ethanol is used as the solvent. The present invention is characterized in that a stirring operation of the raw material and the solvent is carried out under a pressurized state and a temperature condition of 78.3° C. or higher and 130° C. or lower, and then a crystallization operation is carried out by means of a poor solvent method using the raw material solution thus prepared.

The inventor of the present invention found that at the time of preparing the raw material solution, when ethanol was used as the solvent for curcumin or γ-oryzanol and a stirring operation was carried out under a pressurized state and the above-mentioned temperature condition so as not to cause boiling, the highly soluble raw material solution having the solubility of the raw material enhanced could be obtained; and on the basis of this finding, the present invention could be completed.

In the highly soluble raw material solution having the solubility of the raw material enhanced, it is preferable that the solubility thereof be higher than the solubility in each temperature condition shown by the generally known solubility curve of the raw material (curcumin or γ-oryzanol) to ethanol; however, it is especially suitable when it is higher than the solubility under the temperature condition at the time of the crystallization operation and under the pressure condition of a standard atmospheric pressure (1 atm=101.325 kPa). When the temperature condition at the time of the crystallization operation is not lower than 78.3° C., which is a boiling point of ethanol, it is suitable that the solubility of the raw material solution be higher than the solubility under the temperature condition of 75° C. and under the pressure condition of a standard atmospheric pressure (1 atm=101.325 kPa).

With regard to curcumin or γ-oryzanol, when the raw material solution thereof is prepared by using ethanol as the solvent under the above-mentioned condition, a higher concentration of curcumin or γ-oryzanol can be dissolved into ethanol than a usual concentration; and thus, when curcumin or γ-oryzanol is crystallized by means of a poor solvent method using the ethanol solution of curcumin or γ-oryzanol thus prepared, amount of the microparticles of curcumin or γ-oryzanol per one crystallization operation can be increased so that the yield thereof can be enhanced. In addition, it is presumed that the highly soluble raw material solution is in good dissolution condition; and thus microparticles of curcumin or γ-oryzanol with higher uniformity can be produced. Meanwhile, at the time of preparing the ethanol solution of curcumin or γ-oryzanol, it is preferable to use an airtight vessel.

In addition, in the present invention, the temperature of the ethanol solution of curcumin or γ-oryzanol that is prepared in the method described above can be made higher than a prescribed temperature, and it can be used stably in the crystallization operation that follows thereafter. The temperature above this prescribed temperature is dependent on the concentration of the raw material in the ethanol solution, wherein when the curcumin concentration is represented by x (% by weight), this temperature is defined by the temperature y (° C.) described by the formula (1): $y \geq 0.0222x^3 - 2.7x^2 + 30.511x - 12.833$; and when the γ-oryzanol concentration is represented by x (% by weight), this temperature is defined by the temperature y (° C.) described by the formula (2): $y \leq 0.0762x^3 - 0.9429x^2 + 8.8095x + 6 \times 10^{-12}$.

The temperature defined by the formula (1) or the formula (2) includes a temperature which is lower than the dissolution temperature of curcumin or γ-oryzanol into ethanol, wherein even if the temperature of the ethanol solution of curcumin or γ-oryzanol that is prepared in the way as mentioned above is made to the temperature y (° C.) obtained respectively from the formula (1) or the formula (2), the dissolution state of curcumin or γ-oryzanol in ethanol can be stably retained. In addition, the ethanol solution of curcumin or γ-oryzanol that is prepared in the way as mentioned above may be retained for a prescribed period of time at the temperature y (° C.) obtained respectively from the formula (1) or the formula (2).

In the present invention, in view of functionality, the raw material curcumin is preferably at least any one selected from the group consisting of ukon, turmeric, a natural extract from ukon, and a natural extract from turmeric; and the average particle diameter of the curcumin microparticles is preferably in the range of about 30 nm to about 1 μm. Also, in the present invention, in view of functionality, the raw material γ-oryzanol is preferably at least any one selected from the group consisting of a natural extract from a rice bran, a natural extract from a corn oil, and a natural extract from grains; and the average particle diameter of the γ-oryzanol microparticles is preferably in the range of about 30 nm to about 1 μm.

Effects of the Invention

The present invention is characterized by that at the time when the raw material is dissolved into ethanol to prepare the raw material solution, a stirring operation is carried out under the pressurized state and the heated condition, and by carrying out the crystallization operation to the raw material solution thus prepared by means of a poor solvent method, targeted microparticles are efficiently produced. The present invention is superior to conventional methods in the following aspects.

1) Because the dissolution concentration of the raw material in ethanol is increased, use amount of ethanol can be reduced, and the production amount of the target curcumin microparticles or γ-oryzanol microparticles per unit time is increased.
2) Depending on the dissolution concentration of the raw material in ethanol, the retention temperature can be arbitrarily set, and the temperature of the raw material solution during the use time thereof may be set to any temperature so far as it is equal to or higher than the temperature y (° C.) that is defined by the formula (1) or the formula (2), so that it can be used at the temperature of not higher than 78.3° C., which is the boiling point of ethanol; and thus, the handling thereof is easy. Meanwhile, the term "during the use time thereof" means the time during the crystallization operation by means of a poor solvent method using the ethanol solution of curcumin or γ-oryzanol.
3) Contrary to the melting method, use of a high temperature such as 200° C. is not necessary; and thus, it is not necessary to take into consideration denaturation or decomposition of curcumin, γ-oryzanol, or a polymer.
4) As compared with the crushing method, preparation of the solution can be easily done in a short period of time, and there is no contamination of foreign materials derived from the equipment.

As a result of 1) to 4), when the same amount of the curcumin microparticles or of the γ-oryzanol microparticles are produced, the size of the equipment can be significantly reduced.

Figure 1:
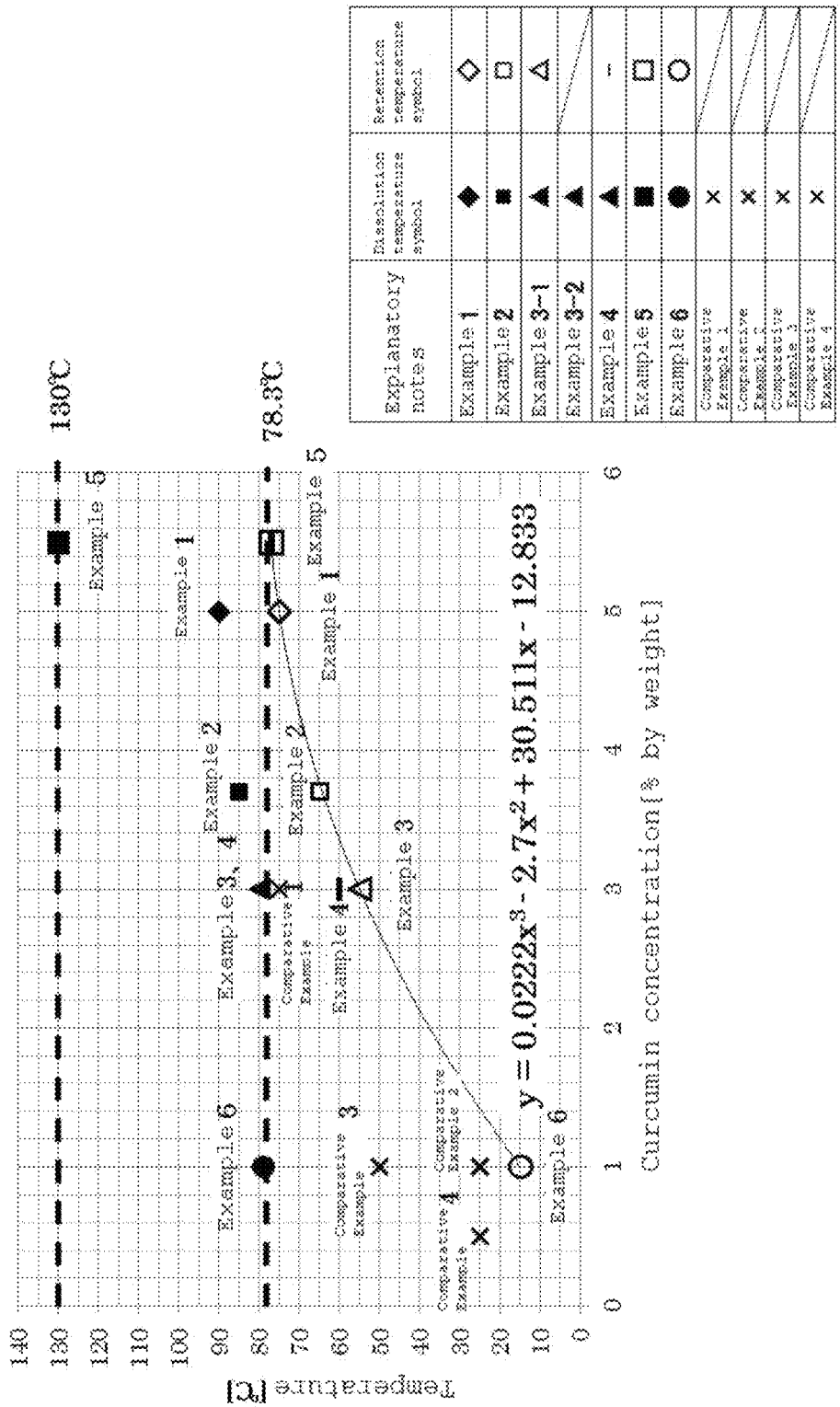
FIG. 1

This is a graph illustrating the relationship of the dissolution temperature of curcumin into ethanol with the curcumin concentration x (% by weight) and with occurrence or non-occurrence of curcumin deposits at the retention temperature (° C.) of the prepared ethanol solution of curcumin.

FIG. 2

This is the TEM picture of the curcumin microparticles produced in Example 1.

FIG. 3

This is a graph illustrating the relationship of the dissolution temperature of γ-oryzanol into ethanol with the γ-oryzanol concentration x (% by weight) and with occurrence or non-occurrence of γ-oryzanol deposits at the retention temperature (° C.) of the prepared ethanol solution of γ-oryzanol.

BEST MODE FOR CARRYING OUT THE INVENTION

Hereinafter, embodiments of the present invention will be explained in detail. Meanwhile, the embodiments of the present invention are not limited to the embodiments described below.

Raw Material

The raw material curcumin used in the present invention is classified as curcuminoid that is obtained from a rhizome of vegetable turmeric belonging to the ginger family. Curcuminoid is a general name of the compounds including curcumin, demethoxy curcumin which is a similar substance to curcumin, and bisdemethoxy curcumin. In the present invention, curcumin may be a single body of curcumin, or may include, together with the curcumin single body, a similar compound thereof such as demethoxy curcumin, bisdemethoxy curcumin, tetrahydro curcumin, dihydroxy tetrahydro curcumin, or the like, or a salt or an ester of these compounds.

In view of functionality, ukon, turmeric, and natural extracts from ukon and turmeric are preferable, but there is no particular restriction, and thus, the present invention can be carried out even with a synthetic substance. When ukon is used, not only a raw ukon but also a dried substance obtained by drying ukon may be used.

The raw material γ-oryzanol used in the present invention is a general name of ferulate esters of triterpene alcohol and of various vegetable sterols, and this is one of biologically active components abundantly included in rice bran. In the present invention, γ-oryzanol may be a substance in which a triterpene alcohol having a steroid skeleton forms an ester bond with ferulic acid. Therefore, illustrative example thereof includes a single body of a cycloarthenol ferulate ester, a campesterol ferulate ester, a β-sitosterol ferulate ester, a cyclobranol ferulate ester, a 24-methylene cycloartanol ferulate ester, and a mixture of these compounds.

In view of functionality, natural extracts from rice bran, from a corn oil, and from other grains are preferable; however, there is no particular restriction; and thus, the present invention can be carried out even with a synthetic substance.

Stirrer

The stirrer to be used in the present invention is not particularly restricted so far as it can stir in an airtight vessel. Illustrative example of the usable stirrer includes a magnetic stirrer, dispersers and emulsifiers such as Clearmix (manufactured by M. Technique Co., Ltd.) and Clearmix Dissolver (manufactured by M. Technique Co., Ltd.), other stirrers, a dissolver, an emulsifier, a disperser, and a homogenizer. When an airtight vessel is not used, the ethanol solution of the raw material (curcumin or γ-oryzanol) boils under the temperature condition above the boiling point thereof to cause evaporation of the ethanol solvent; and thus, there is a risk of the change in the concentration of the raw material in the solution. In addition, there is a risk of explosion or the like because ethanol is a flammable substance. Therefore, it is preferable to dissolve the raw material into ethanol by using an airtight vessel.

Ethanol Solution

To produce the curcumin microparticles or the γ-oryzanol microparticles by using the ethanol solution of curcumin or γ-oryzanol has a high practical value in view of residual solvent and safety when these microparticles are used in food additives, medical drugs, or health drinks. Meanwhile, ethanol is described as the solvent that is considered to have low toxicity and low risk to human health as defined in class 3 in "Guideline for Residual Solvents in Pharmaceuticals" (Pharmaceutical Affairs Bureau Notification No. 307; dated Mar. 30, 1998). On the other hand, with regard to the solvents other than ethanol, acetone and the like are also defined as class 3, so that these solvents may also be possibly used as the solvent to dissolve the raw material curcumin or γ-oryzanol. However, even if these solvents are defined as class 3, many of them lack the long term toxicity test and carcinogenicity test, so that the solvent that is ensured with safety in steady use as foods is very rare. For example, acetone is classified as class 3 in "Guideline for Residual Solvents in Pharmaceuticals", but when this is used in foods, there is a possibility of a large intake thereof. Therefore, even though it is classified as class 3, the residual solvent included in foods is regulated to a lower value as compared when it is used only in medical drugs.

Accordingly, not only there is a chance of having a large daily intake but also there is a chance of steady use as foods; therefore, considering the safety and the like when total intake amount thereof, for example, through a year is large, it can be said that ethanol is the most preferable solvent to be used for dissolution of curcumin or γ-oryzanol.

Additives, Etc.

In addition, at the time when the raw material (curcumin or γ-oryzanol) is dissolved into ethanol, among other things, a cellulose such as hydroxymethyl cellulose, hydroxypropyl methyl cellulose, or hydroxypropyl cellulose, or a polymer such as polyvinyl alcohol, polyvinyl pyrrolidone, polylactic acid, polyglycolic acid, or poly(lactic acid-glycolic acid) copolymer may be added to ethanol.

In addition, at the time when the raw material is dissolved into ethanol, as the case may be, an organic acid such as acetic acid or citric acid, or a solvent such as a glycol-type solvent, for example, ethylene glycol or propylene glycol, may also be added to ethanol.

It is preferable to select these substances that have been actually used as a food additive or those that are described in the encyclopedia of pharmaceutical additives, when it is used.

These substances are added to ethanol at the time when the curcumin microparticles or the γ-oryzanol microparticles are obtained by the crystallization operation by means of a poor solvent method to be described later, with an aim to suppress growth of these microparticles. For example, a cellulose, a polymer, or a glycol-type solvent is used as the surface protection agent of the particles, and an organic acid is used as the growth suppressing agent of the same.

Dissolution Conditions

With regard to the dissolution temperature of the raw material including curcumin or γ-oryzanol into ethanol, in order to increase solubility of the raw material into ethanol, the dissolution is carried out preferably at the temperature of not lower than 78.3° C., which is a standard boiling point of ethanol, and 130° C. or lower, while more preferably at the temperature of 80° C. or higher and 100° C. or lower.

If the dissolution temperature of the raw material into ethanol is made to 130° C. or higher, there is a possibility of partial decomposition of curcumin or γ-oryzanol. In addition, if the dissolution temperature of the raw material into ethanol is made to 130° C. or higher, because of the vapor pressure of ethanol the equipment needs to be made thicker, so that this is not practical.

The stirring time of the ethanol solution at the time of preparation of the ethanol solution of the raw material is not particularly restricted. However, there is a risk of partial decomposition of the raw material when the stirring operation is carried out at high temperature for a long period of time; and thus, the stirring time is preferably within 3 hours, while more preferably within 1 hour.

Dissolution of the raw material into ethanol is carried out preferably at the temperature of equal to or higher than a standard boiling point of ethanol and the temperature equal to or lower than a boiling point of ethanol under a pressurized condition. When the dissolution of the raw material is carried out under a pressurized condition, even if the temperature becomes higher than the standard boiling point of the ethanol solution of the raw material, the dissolution of the raw material into ethanol can be carried out stably at the temperature of equal to or higher than the standard boiling point thereof without causing boiling. By so doing, a large quantity of energy such as a thermal energy can be given to the raw material and ethanol necessary for dissolution of the raw material into the ethanol solution.

Meanwhile, in the present invention, the boiling point means the temperature at the time when both the saturated vapor and the liquid phase thereof co-exist in an equilibrium state under a certain pressure; and the standard boiling point means the boiling point at the pressure of 1 atm.

When the dissolution of the raw material into ethanol is carried out under the pressurized state and the temperature condition of 78.3° C. or higher and 130° C. or lower, the raw material can be dissolved into ethanol even with the concentration thereof being more than 5% by weight. Considering that the solubility of the raw material in ethanol at 25° C. is about 0.5% by weight, this is a very surprising result.

In addition, the ethanol solution of curcumin and the ethanol solution of γ-oryzanol prepared in the way as described above can be stably used above a prescribed temperature in the precipitation operation that follows thereafter. The temperature y (° C.) equal to and above the prescribed temperature is dependent on the raw material in the ethanol solution of curcumin and the ethanol solution of γ-oryzanol (curcumin concentration and γ-oryzanol concentration), wherein when the curcumin concentration is represented by x (% by weight), this temperature is defined by:

$$y \geq 0.0222x^3 - 2.7x^2 + 30.511x - 12.833 \quad (1)$$

and when the γ-oryzanol concentration is represented by x (% by weight), this temperature is defined by:

$$y \geq 0.0762x^3 - 0.9429x^2 + 8.8095x + 6 \times 10^{-12} \quad (2)$$

The temperature defined by the formula (1) or the formula (2) includes the temperature lower than the dissolution temperature of curcumin or γ-oryzanol into ethanol; however, even if the temperature of the ethanol solution of curcumin or of γ-oryzanol that is prepared in the way as described above is made to the temperature defined by the formula (1) or (2), curcumin or γ-oryzanol in the ethanol solution does not separate, so that the dissolution state of curcumin or of γ-oryzanol in ethanol can be stably retained. In addition, the ethanol solution of curcumin or γ-oryzanol that is prepared in the way as described above may be retained for a prescribed period of time at the temperature y (° C.) that is defined by the formula (1) or (2), respectively. Below this temperature y (° C.), separation takes place partially; but after operation of filtration or the like, this can be used in the crystallization that follows thereafter. After curcumin or γ-oryzanol is dissolved in ethanol, when this ethanol solution is used in the crystallization operation by means of a poor solvent method under the condition as it is dissolved in the dissolution condition of the heated and pressurized state, the production efficiency thereof can be significantly increased. The prescribed period of time is not particularly restricted; however, considering the possibility of partial decomposition of curcumin or γ-oryzanol by a UV beam or a visible light when curcumin or γ-oryzanol is retained under the state of being dissolved in ethanol for a long period of time, the prescribed period of time within 8 hours is preferable, while within 3 hours is more preferable.

In addition, after curcumin or γ-oryzanol is dissolved in ethanol, by sending the resulting solution to the fluid processing apparatus based on the same principle as the one described in Japanese Patent Laid-Open Publication No. 2011-189348 as it is in the heated and pressurized state, which is the dissolution condition thereof, this solution can be used in the crystallization operation by means of a poor solvent method. By using this method, preparation of the raw material solution and crystallization in the fluid processing apparatus can be carried out continuously, so that the production efficiency thereof can be significantly increased.

With Regard to Dissolution of Curcumin

The inventor of the present invention presumed that when the raw material curcumin is dissolved in ethanol by mixing curcumin with ethanol under the pressurized state and at the temperature of not lower than 78.3° C., which is the standard boiling point of ethanol, the kinetic energy of the ethanol molecule under the high temperature and pressurized state is increased as compared with the kinetic energy of the ethanol molecule under the normal temperature and normal pressure, so that the ethanol molecule having a large kinetic energy acts to the curcumin molecule thereby giving an energy to the curcumin molecule; and furthermore, by carrying out the stirring operation, the curcumin molecule and the ethanol molecule are uniformly stirred thereby resulting in the state that dissolution of the curcumin molecule into the ethanol molecule is facilitated. In addition, it is presumed that by mixing the raw material curcumin with ethanol at the temperature higher than the standard boiling point of ethanol and under the pressurized condition, the interaction between the OH group of the curcumin molecule and the OH group of ethanol is increased thereby leading to enhancement of the stability during dissolution of curcumin into ethanol. This is presumably because curcumin has two tautomers of a keto form and an enol form and whereby the keto form and the enol form always interchange therebetween, and thus, as the temperature is raised, the enol form increases thereby leading to increase in the interaction between the enol form and ethanol. Under the state like this, the dissolution state of curcumin in ethanol can be stabilized; and thus, narrowing of the width was confirmed in the particle diameter distribution of the curcumin microparticles obtained in the crystallization operation by means of a poor solvent method to be described later.

In addition, it is presumed that by retaining the prepared ethanol solution of curcumin at the temperature y (° C.) as defined in the formula (1), the interaction (hydrogen bonding) between curcumin and ethanol is enhanced as compared with the interaction among ethanol, so that the dissolution state of curcumin in ethanol can be stably retained. Curcumin has two tautomers of a keto form and an enol form; and thus, it is presumed that as the temperature is raised the enol form increases thereby leading to increase in the interaction between the enol form and ethanol, so that the dissolution state thereafter can be stably retained. Although a clear reason is not known yet, it is presumed that because the interaction (hydrogen bonding) generated at the high temperature is retained for a while even when the temperature is lowered, the dissolution state of curcumin in ethanol can be stabilized thereby leading to the state that separation of curcumin is difficult.

With Regard to Dissolution of γ-Oryzanol

The inventor of the present invention presumed that when the raw material γ-oryzanol is dissolved in ethanol by mixing γ-oryzanol with ethanol under the pressurized state and at the temperature of not lower than 78.3° C., which is the standard boiling point of ethanol, the kinetic energy of the ethanol molecule under the high temperature and pressurized state is increased as compared with the kinetic energy of the ethanol molecule under the normal temperature and normal pressure, so that the ethanol molecule having a large kinetic energy acts to the γ-oryzanol molecule thereby giving an energy to the γ-oryzanol molecule; and furthermore, by carrying out the stirring operation, the γ-oryzanol molecule and the ethanol molecule are uniformly stirred thereby resulting in the state that dissolution of the γ-oryzanol molecule into the ethanol molecule is facilitated. It is presumed that when γ-oryzanol is in the solid state, γ-oryzanol is in a structure that the γ-oryzanol molecules are regularly arranged; and when it is heated under the pressurized state, the ethanol molecule penetrates into the structure thereby generating the interaction including the hydrogen bonding between the γ-oryzanol molecule and ethanol so that stability at the time of dissolution into ethanol is enhanced. Under the state like this, the dissolution state of γ-oryzanol in ethanol can be stabilized; and thus, narrowing of the width was confirmed in the particle diameter distribution of the γ-oryzanol microparticles obtained in the crystallization operation by means of a poor solvent method to be described later.

In addition, in the prepared solution of γ-oryzanol, it is presumed that the interaction (hydrogen bonding) between γ-oryzanol and ethanol is enhanced as compared with the interaction among ethanol. Therefore, the dissolution state of γ-oryzanol in ethanol can be stably retained so far as the solution is retained at the temperature y (° C.) as defined in the formula (2). Although a clear reason is not known yet, it is presumed that because the interaction (hydrogen bonding) generated at the high temperature is retained for a while even when the temperature is lowered, the dissolution state of γ-oryzanol in ethanol can be stabilized thereby leading to the state in which separation of γ-oryzanol is difficult.

Crystallization Operation

With regard to the method to obtain the target microparticles (curcumin microparticles or γ-oryzanol microparticles) with the crystallization operation by means of a poor solvent method using the raw material solution having the raw material (curcumin or γ-oryzanol) dissolved in ethanol, there is no particular restriction, so that various methods may be used. Illustrative example of the usable method includes a method in which mixing of the raw material solution with a poor solvent is carried out in a mixing vessel of a batch-type and a method in which the raw material solution is mixed with a poor solvent by using reacting equipment such as a micro reactor. In view of uniformity of the particle diameter and the control thereof, it is preferable to prepare the target microparticles by using the apparatus based on the same principle as the fluid processing apparatus which is proposed by the applicant of the present invention and is described in Japanese Patent Laid-Open Publication No. 2011-189348. Specifically, the fluid processing apparatus is used wherein the apparatus is provided with at least two processing surfaces which rotate relative to each other, and the at least two processing surfaces are arranged such that they can relatively approach to and separate from each other in the axial direction of the rotation. In this case, the at least two processing surfaces retain a minute clearance therebetween; and the poor solvent and the raw material solution are introduced into between the at least two processing surfaces retaining the minute clearance therebetween. Upon introduction, it is preferable to introduce the poor solvent and the raw material solution into between the at least two processing surfaces through separate, independent introduction paths; however, it is also allowed to use the method in which the poor solvent and the raw material solution are mixed just before introducing into the apparatus, and then, the solution thus mixed is introduced into between the at least two processing surfaces so as to receive the mixing action in a forced thin film in the at least two processing surfaces. In the case when the apparatus having two introduction paths is used, it is preferable that one introduction path be arranged in a central part of at least one processing surface of the two processing surfaces, and the other introduction path be arranged between the one introduction path and the outer circumference of the at least two processing surfaces in a radius direction. By so doing, the forced thin film by the mixed solution of the poor solvent and the raw material solution is formed between the at least two processing surfaces, and the target microparticles are crystallized in this forced thin film. At this time, when the raw material solution with the temperature thereof being y (° C.) as obtained by the formula (1) or (2) is introduced into between the at least two processing surfaces, the target microparticles can be obtained uniformly and stably. In addition, after the raw material solution is retained at the temperature y (° C.) as obtained by the formula (1) or (2) for a prescribed period of time, by raising the temperature of the raw material solution to a temperature higher than the retention temperature y (° C.), the raw material solution can be introduced into the at least two processing surfaces under a more uniform state thereof.

Poor Solvent

With regard to the poor solvent, there is no particular restriction so far as it has a lower solubility to the raw material (curcumin or γ-oryzanol) as compared with the raw material solution, namely the ethanol solution of the raw material (curcumin or γ-oryzanol). In view of the residual solvent and the safety thereof in the obtained target microparticles (curcumin microparticles or γ-oryzanol microparticles), it is preferable to use water as the poor solvent. Illustrative example of this water includes natural water, tapped water, ion-exchanged water, purified water, ultra-purified water, and distilled water. Besides, linear alkanes such as hexane, heptane, and octane, as well as cycloalkanes such as cyclohexane may be used as the poor solvent.

In addition, a cellulose such as hydroxymethyl cellulose, hydroxypropyl methyl cellulose, or hydroxypropyl cellulose; a polymer such as polyvinyl alcohol or polyvinyl pyrrolidone; an organic acid such as acetic acid or citric acid; a saccharide such as gum Arabic, maltose, D-mannitol, glucose, or fructose; or denatured starch, sodium chloride, L-ascorbic acid, vitamin A, or the like may be added to the poor solvent. It is preferable to select the substance which has been actually used as a food additive or which is described in the encyclopedia of pharmaceutical additives, when it is used.

At the time when the target microparticles are obtained by the crystallization operation by means of the poor solvent method, some of these substances are added to the poor solvent with an aim to suppress growth of the target microparticles. For example, the celluloses, the polymers, and the glycol-type solvents are used as the surface protection agent of the target microparticles obtained in the crystallization operation, and the organic acids and sodium chloride are used as the growth suppressing agent.

By adding the organic acid to any one of the raw material solution and the poor solvent or both, pH of the mixed solution is made to an acidic side in the crystallization operation by means of the poor solvent method thereby decreasing the dissolution concentration of the raw material in the mixed solution, so that growth of the crystallized target microparticles is suppressed. Also, by adding sodium chloride to the poor solvent thereby decreasing the dissolution concentration of the raw material in the mixed solution, growth of the crystallized target microparticles is suppressed.

The average particle diameter of the target microparticles is preferably in the unit of nanometer, but it may be in the unit of micrometer. It is preferable that the average particle diameter of the target microparticles be in the range of 30 nm to 1 μm.

EXAMPLES

Hereinafter, the present invention will be explained more specifically by referring to Examples. However, the present invention is not limited to the Examples. In the Examples, for preparation of the ethanol solution of the raw material curcumin or preparation of the ethanol solution of the raw material γ-oryzanol, Clearmix (manufactured by M. Technique Co., Ltd.), Clearmix Dissolver, or a magnetic stirrer was used. For production of the curcumin microparticles or the γ-oryzanol microparticles, the fluid processing apparatus described in Japanese Patent Laid-Open Publication No. 2011-189348 was used. However, the apparatus to be used for production of the curcumin microparticles or the γ-oryzanol microparticles of the present invention is not limited to this apparatus.

For TEM observation, a transmission electron microscope (JEM-2100; manufactured by JEOL Ltd.) was used. The observation conditions with 80 kV of the acceleration voltage and 10000 or more of the observation magnification were used.

With regard to the average particle diameter of the curcumin microparticles or the γ-oryzanol microparticles, the average value of 50 particles recognized in the TEM picture with the magnification of 25000 was used. The average particle diameter of the curcumin microparticles is described in the item "Particle diameter" in Table 1; and the average particle diameter of the γ-oryzanol microparticles is described in the item "Particle diameter" in Table 2.

Preparation of the Ethanol Solution of Curcumin

First, the method for preparation of the ethanol solution of curcumin and the method for retention of the prepared ethanol solution of curcumin at a prescribed temperature will be explained. Hereinafter, the ethanol solution of curcumin that is retained at a prescribed temperature is referred to as the ethanol solution of curcumin after preparation. Meanwhile, the prescribed temperature is the temperature y (° C.) that is obtained by the formula (1).

In Examples, the used curcumin was curcumin (Wako special grade) manufactured by Wako Pure Chemical Industries, Ltd., and the used ethanol was ethanol (special reagent grade) manufactured by Wako Pure Chemical Industries, Ltd.

Hereinafter, "inside the vessel" means inside the airtight vessel, "pressure inside the vessel" means the pressure inside the airtight vessel, and "temperature inside the vessel" means the temperature inside the airtight vessel.

Example 1

In Example 1, curcumin and ethanol each were weighed so as to give the ethanol solution of curcumin with the concentrations of curcumin and ethanol being respectively 5% by weight and 95% by weight, and then the ethanol solution thus obtained with the total weight of 700 g was taken into a 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm. At this time, the dissolution treatment of curcumin into ethanol was carried out with the dissolution temperature of 90° C. and with the pressure inside the vessel (pressure inside the attachment) of 0.09 MPaG.

After 30 minutes since the temperature inside the vessel reached 90° C., the rotation number of the rotor was changed to 4500 rpm, and the solution was cooled to 76° C. Then, the ethanol solution of 5% by weight of curcumin and 95% by weight of ethanol was taken out from the attachment, and it was confirmed with a visual observation that curcumin was dissolved in ethanol. Then, the prepared ethanol solution of curcumin was transferred to a glass vessel. When the ethanol solution of curcumin in the glass vessel was retained in a water bath at 75° C. for 1 hour, it was confirmed with a visual observation that there was no deposit. Temperature of the ethanol solution of curcumin after being retained in the water bath at 75° C. for 1 hour (ethanol solution of curcumin after preparation) was 75° C.

Example 2

In Example 2, curcumin and ethanol each were weighed so as to give the ethanol solution of curcumin with the concentrations of curcumin and ethanol being respectively 3.7% by weight and 96.3% by weight, and then the ethanol solution thus obtained with the total weight of 700 g was taken into the 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm. At this time, the dissolution treatment of curcumin into ethanol was carried out with the dissolution temperature of 85° C. and with the pressure inside the vessel (pressure inside the attachment) of 0.09 MPaG.

After 30 minutes since the temperature inside the vessel reached 85° C., the rotation number of the rotor was changed to 4500 rpm, and the solution was cooled to 70° C. Then, the ethanol solution of 3.7% by weight of curcumin and 96.3% by weight of ethanol was taken out from the attachment, and it was confirmed with a visual observation that curcumin was dissolved in ethanol. Then, the prepared ethanol solution of curcumin was transferred to a glass vessel. When the ethanol solution of curcumin in the glass vessel was retained in a water bath at 65° C. for 1 hour, it was confirmed with a visual observation that there was no deposit. Temperature of the ethanol solution of curcumin after being retained in the water bath at 65° C. for 1 hour (ethanol solution of curcumin after preparation) was 65° C.

Example 3-1

In Example 3-1, curcumin and ethanol each were weighed so as to give the ethanol solution of curcumin with the concentrations of curcumin and ethanol being respectively 3% by weight and 97% by weight, and then the ethanol solution thus obtained with the total weight of 700 g was taken into an airtight vessel. The stirring operation under the heated and pressurized state was carried out for 2 hours by using a magnetic stirrer with a 5-cm stirrer chip with the rotation number of 1000 rpm, and with the dissolution temperature of 80° C. and the pressure inside the vessel of 0.06 MPaG upon dissolution. After the prepared ethanol solution of curcumin was cooled to 60° C., it was confirmed that there was no deposit. When the ethanol solution of curcumin was retained in a water bath at 55° C. for 1 hour, it was confirmed that there was no deposit. Temperature of the ethanol solution of curcumin after being retained in the water bath at 55° C. for 1 hour (ethanol solution of curcumin after preparation) was 55° C.

Example 3-2

In Example 3-2, the ethanol solution of curcumin was prepared under the same condition as Example 3-1. After the prepared ethanol solution of curcumin was cooled to 70° C., it was confirmed that there was no deposit. Then, the crystallization operation to be described later was carried out without retaining the prepared ethanol solution of curcumin at the prescribed temperature.

Example 4

In Example 4, curcumin and ethanol each were weighed so as to give the ethanol solution of curcumin with the concentrations of curcumin and ethanol being respectively 3% by weight and 97% by weight, and then the ethanol solution thus obtained with the total weight of 700 g was taken into the airtight vessel. The stirring operation under the heated and pressurized state was carried out by using Clearmix Dissolver (product name: CLM-2.2SD, manufactured by M. Technique Co., Ltd.) with the rotation number of the rotor thereof being 10000 rpm, the dissolution temperature of 80° C., and the pressure inside the vessel of 0.06 MPaG so as to carry out the dissolution treatment of curcumin into ethanol. After 30 minutes since the temperature inside the vessel reached 80° C., the rotation number of the rotor was changed to 4500 rpm, and the solution was cooled to 70° C. Then, the ethanol solution of 3% by weight of curcumin and 97% by weight of ethanol was transferred to a glass vessel, and it was confirmed that there was no deposit. When the ethanol solution of curcumin in the glass vessel was retained in a water bath at 60° C. for 1 hour, it was confirmed that there was no deposit. Temperature of the ethanol solution of curcumin after being retained in the water bath at 60° C. for 1 hour was 60° C.

Example 5

In Example 5, curcumin and ethanol each were weighed so as to give the ethanol solution of curcumin with the concentrations of curcumin and ethanol being respectively 5.5% by weight and 94.5% by weight, and then the ethanol solution thus obtained with the total weight of 700 g was taken into the 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 20000 rpm with the dissolution temperature of 130° C. and with the pressure inside the vessel of 0.55 MPaG so as to carry out the dissolution treatment of curcumin into ethanol.

After 30 minutes since the temperature inside the vessel reached 130° C., the rotation number of the rotor was changed to 4500 rpm, and the solution was cooled to 78° C. Then, the ethanol solution of 5.5% by weight of curcumin and 94.5% by weight of ethanol was transferred to a glass vessel, and it was confirmed that there was no deposit. When the ethanol solution of curcumin in the glass vessel was retained in a water bath at 77° C. for 1 hour, it was confirmed that there was no deposit. Temperature of the ethanol solution of curcumin after being retained in the water bath at 77° C. for 1 hour (ethanol solution of curcumin after preparation) was 77° C.

Example 6

In Example 6, curcumin and ethanol each were weighed so as to give the ethanol solution of curcumin with the concentrations of curcumin and ethanol being respectively 1.0% by weight and 99.0% by weight, and then the ethanol solution thus obtained with the total weight of 700 g was taken into the 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm, the dissolution temperature of 79° C., and the pressure inside the vessel of 0.06 MPaG so as to carry out the dissolution treatment of curcumin into ethanol.

After 30 minutes since the temperature inside the vessel reached 79° C., the rotation number of the rotor was changed to 4500 rpm, and the solution was cooled to 20° C. Then, the ethanol solution of 1.0% by weight of curcumin and 99.0% by weight of ethanol was transferred to a glass vessel, and it was confirmed that there was no deposit. When the ethanol solution of curcumin in the glass vessel was retained at 15.1° C. for 1 hour, it was confirmed that there was no deposit. Temperature of the ethanol solution of curcumin after being retained in the water bath at 15.1° C. for 1 hour (ethanol solution of curcumin after preparation) was 15.1° C.

As Comparative Example 1, curcumin and ethanol each were weighed so as to give the ethanol solution of curcumin with the concentrations of curcumin and ethanol being respectively 3% by weight and 97% by weight, and then the prepared ethanol solution with the total weight of 700 g was taken into the 1000-cc attachment. The dissolution treatment of curcumin into ethanol was carried out by using Clearmix (product name: CLM-2.2S, manufactured by M. Technique Co., Ltd.) with the rotation number of the rotor thereof being 10000 rpm, the dissolution temperature of 75° C., and the pressure inside the vessel of 0.06 MPaG. After 30 minutes of stirring at 75° C., when dissolution of curcumin was checked with a visual observation, it was confirmed that there existed undissolved curcumin in the ethanol solution. Because the undissolved curcumin was confirmed in the ethanol solution of curcumin, the subsequent operations were not carried out.

As Comparative Example 2, curcumin and ethanol each were weighed so as to give the ethanol solution of curcumin with the concentrations of curcumin and ethanol being respectively 1.0% by weight and 99.0% by weight, and then the ethanol solution thus obtained with the total weight of 700 g was taken into the 1000-cc attachment. The dissolution treatment of curcumin into ethanol was carried out by using Clearmix (product name: CLM-2.2S, manufactured by M. Technique Co., Ltd.) with the rotation number of the rotor thereof being 10000 rpm, the dissolution temperature of 25° C., and the pressure inside the vessel of 0.00 MPaG. After 30 minutes of stirring at 25° C., when dissolution of curcumin was checked with a visual observation, it was confirmed that there existed undissolved curcumin in the ethanol solution. Because the undissolved curcumin was confirmed in the ethanol solution of curcumin, the subsequent operations were not carried out.

As Comparative Example 3, curcumin and ethanol each were weighed so as to give the ethanol solution of curcumin with the concentrations of curcumin and ethanol being respectively 1.0% by weight and 99.0% by weight, and then the ethanol solution thus obtained with the total weight of 700 g was taken into the 1000-cc attachment. The dissolution treatment of curcumin into ethanol was carried out by using Clearmix (product name: CLM-2.2S, manufactured by M. Technique Co., Ltd.) with the rotation number of the rotor thereof being 10000 rpm, the dissolution temperature of 50° C., and the pressure inside the vessel of 0.00 MPaG. After 30 minutes of stirring at 50° C., when dissolution of curcumin was checked with a visual observation, it was confirmed that there existed undissolved curcumin in the ethanol solution. Because the undissolved curcumin was confirmed in the ethanol solution of curcumin, the subsequent operations were not carried out.

As Comparative Example 4, curcumin and ethanol each were weighed so as to give the ethanol solution of curcumin with the concentrations of curcumin and ethanol being respectively 0.5% by weight and 99.5% by weight, and then the obtained ethanol solution with the total weight of 700 g was taken into the 1000-cc attachment. The dissolution treatment of curcumin into ethanol was carried out by using Clearmix (product name: CLM-2.2S, manufactured by M. Technique Co., Ltd.) with the rotation number of the rotor thereof being 10000 rpm, the dissolution temperature of 25° C., and the pressure inside the vessel of 0.00 MPaG. After 30 minutes of stirring at 25° C., it was confirmed with a visual observation that curcumin was dissolved in ethanol.

Crystallization Operation by Means of the Poor Solvent Method

Next, in each Example, the curcumin microparticles were prepared by means of the poor solvent method using the ethanol solution of curcumin after preparation (in Example 3-2, the prepared ethanol solution of curcumin) and the poor solvent described in Table 1. For preparation of the poor solvent, Clearmix (product name: CLM-2.2S, manufactured by M. Technique Co., Ltd.) was used. The stirring was carried out at a room temperature and under a standard pressure (namely, 1 atm=0.101325 MPa) with the rotation number of the rotor thereof being 15000 rpm for 30 minutes. Meanwhile, HPMC described in Table 1 is the abbreviation of hydroxypropyl methyl cellulose, one of water-soluble polymers, wherein Metolose (trade name) manufactured by Shin-Etsu Chemical Co., Ltd. was used. With regard to the acetic acid described in Table 1, acetic acid (special reagent grade) manufactured by Wako Pure Chemical Industries, Ltd. was used.

The ethanol solution of curcumin after preparation and the poor solvent after preparation were mixed by using the fluid processing apparatus described in Japanese Patent Laid-Open Publication No. 2011-189348. Meanwhile, the fluid processing apparatus described in Japanese Patent Laid-Open Publication No. 2011-189348 is the one described in FIG. 25 of the said gazette, wherein the opening d20 of the second introduction part is in a concentric circular form surrounding the central opening of the processing surface 2 which is a ring-like disc. Specifically, the poor solvent after preparation was introduced from the first introduction part d1 into between the processing surfaces 1 and 2 at about 0.1 MPaG to about 0.2 MPaG, 450 mL/minute, and 20° C.; and with operating the processing member 10 with the rotation number each described in Table 1, the ethanol solution of curcumin after preparation was introduced from the second introduction part d2 into between the processing surfaces 1 and 2 at about 0.1 MPaG to about 0.2 MPaG, 150 mL/minute, and at 75° C. in Example 1, at 70° C. in Examples 2 to 6, and at 25° C. in Comparative Example 4, thereby the both fluids were mixed in the forced thin film to crystallize the curcumin microparticles between the processing surfaces 1 and 2. The fluid including the curcumin microparticles crystallized between the processing surfaces 1 and 2 (hereinafter, this fluid is referred to as the curcumin microparticles dispersion solution) was ejected from between the processing surfaces 1 and 2 of the fluid processing apparatus. Then, the curcumin microparticles dispersion solution was recovered in the beaker via the vessel to collect the curcumin microparticles dispersion solution thus ejected.

Figure 2:
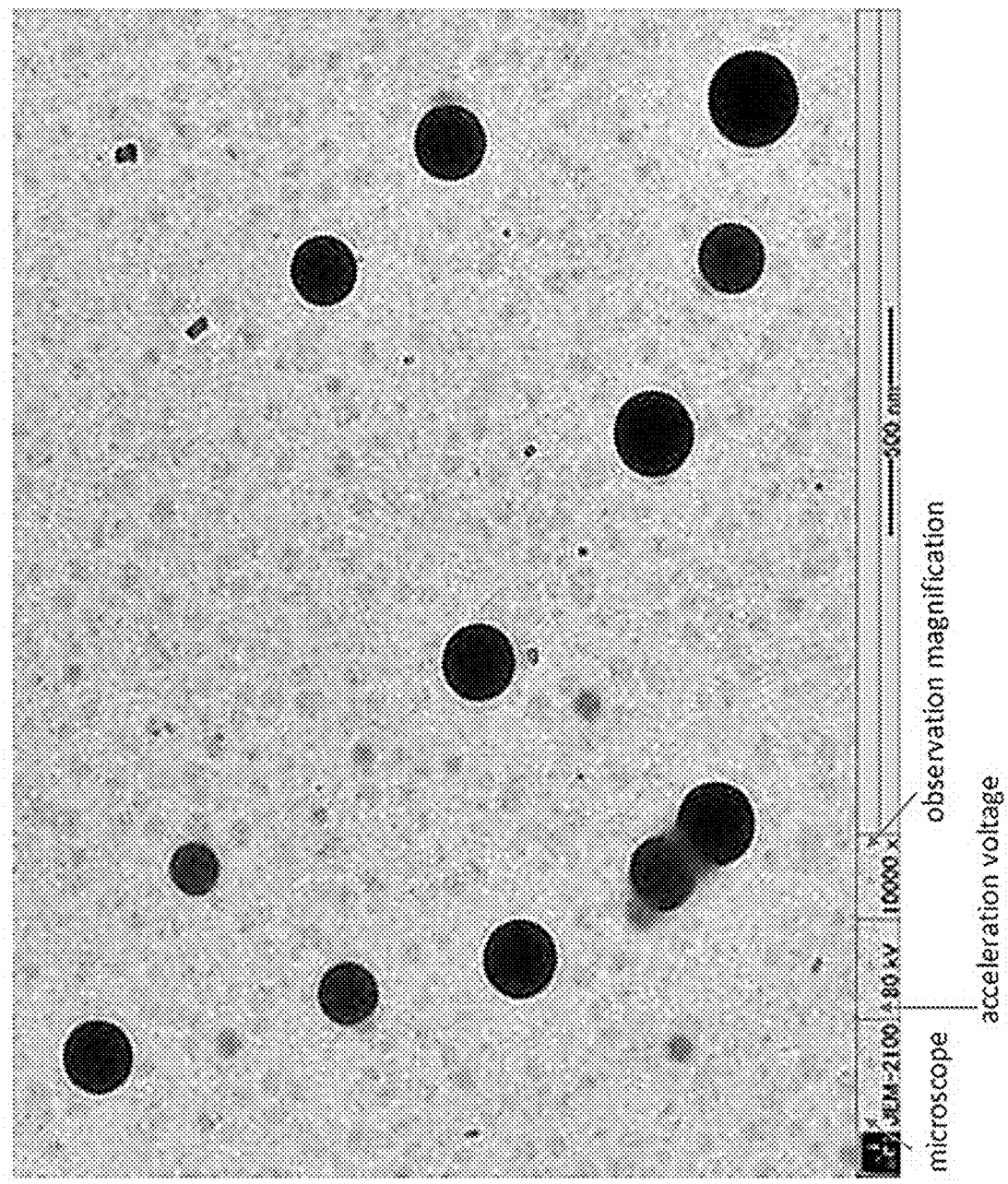
Figure 3:
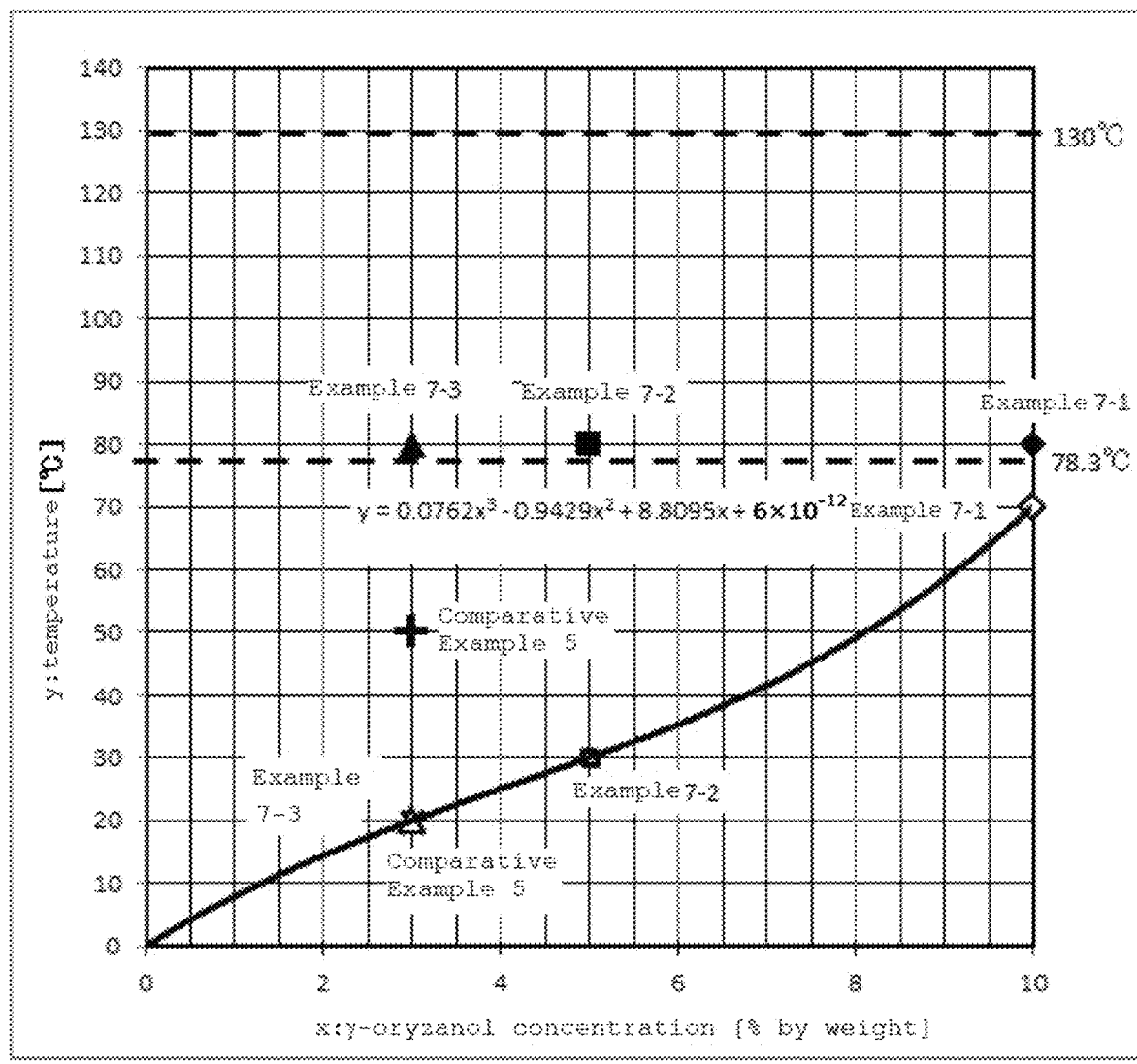

The curcumin microparticles dispersion solution thus produced using the above-mentioned apparatus was dropped onto an ester supporting film, and then it was dried at room temperature to obtain the sample for the TEM observation. The TEM observation result of Example 1 is illustrated in FIG. 2.

The preparation conditions of the ethanol solution of curcumin, the retention temperature of the ethanol solution of curcumin, the prescription of the poor solvent, the crystallization conditions of the curcumin microparticles, and the particle diameter of the obtained curcumin microparticles are summarized in Table 1.

TABLE 1

| | Ethanol solution of curcumin | | | | | | | | | |
|---|---|---|---|---|---|---|---|---|---|---|
| | Preparation condition | | | | | | Retention condition | Crystallization operation by the poor solvent | | |
| | Concentration of curcumin [wt %] | Dissolution temperature [° C.] | Pressure inside the vessel [MPaG] | Retention time at the time of Dissolution [min] | Rotation number at the time of Dissolution [rpm] | Dissolution | Retention temperature [° C.] | Deposit; Yes/No | Poor solvent | Rotation number [rpm] | Particle diameter [nm] |
| Example 1 | 5 | 90 | 0.09 | 30 | 10000 | O | 75 | No | 0.67 wt % HPMC/ 99.33 wt % pure water | 1000 | 120 |
| Example 2 | 3.7 | 85 | 0.09 | 30 | 10000 | O | 65 | No | 99.33 wt % pure water | 1000 | 130 |
| Example 3-1 | 3 | 80 | 0.06 | 120 | 1000 | O | 55 | No | 0.80 wt % HPMC/ 0.005 wt % citric acid/ 99.195 wt % pure water | 500 | 110 |
| Example 3-2 | | | | | | | — | — | | 500 | 110 |
| Example 4 | 3 | 80 | 0.06 | 30 | 10000 | O | 60 | No | 0.67 wt % HPMC/ 0.0009 wt % acetic acid/ 99.3291 wt % pure water | 1000 | 52 |
| Example 5 | 5.5 | 130 | 0.55 | 30 | 20000 | O | 77 | No | 0.67 wt % HPMC/ 1.0 wt % acetic acid/ 98.33 wt % pure water | 1000 | 970 |
| Example 6 | 1 | 79 | 0.06 | 30 | 10000 | O | 15.1 | No | 0.67 wt % HPMC/ 1.0 wt % acetic acid/ 98.33 wt % pure water | 500 | 680 |
| Comparative Example 1 | 3 | 75 | 0.06 | 30 | 10000 | X | — | — | — | — | — |
| Comparative Example 2 | 1 | 25 | 0 | 30 | 10000 | X | — | — | — | — | — |
| Comparative Example 3 | 1 | 50 | 0 | 30 | 10000 | X | — | — | — | — | — |
| Comparative Example 4 | 0.5 | 25 | 0 | 30 | 10000 | O | — | — | 0.67 wt % HPMC/ 99.33 wt % pure water | 1000 | 110 |

With regard to the item of "Dissolution" described in Table 1, whether or not the curcumin was dissolved in ethanol was confirmed with a visual observation. When deposit or the curcumin undissolved in the ethanol solution of curcumin was confirmed with the visual observation, this was designated with "X", and when curcumin was not confirmed with the visual observation in the ethanol solution, this was designated as "O".

With regard to whether deposit was present or not in the ethanol solution of curcumin, after the prepared ethanol solution of curcumin was retained at the prescribed temperature for 1 hour, confirmation thereof was made with the visual observation; and the result thereof is described in the item of "Deposit; Yes/No" described in Table 1.

As the result of the above, at the time when the ethanol solution of curcumin was prepared by dissolving curcumin into ethanol, in the case where the stirring operation was carried out under the pressurized state and the temperature condition of 78.3° C. or higher and 130° C. or lower, deposit was not confirmed in the prepared ethanol solution of curcumin. When the crystallization operation was carried out by means of the poor solvent method using the prepared ethanol solution of curcumin, the average particle diameter of the obtained curcumin microparticles was 1 μm or less.

Especially, when the prepared ethanol solution of curcumin was retained for a prescribed period of time at the temperature y (° C.) defined by the formula (1), the dissolution state of curcumin in ethanol could be stably retained; and thus, in the crystallization operation by means of the poor solvent method subsequently followed, it was confirmed that uniform curcumin microparticles could be prepared as well.

On the other hand, at the time when the ethanol solution of curcumin was prepared by dissolving curcumin into ethanol, in the case where the stirring operation was carried out under the temperature condition of lower than 78.3° C., curcumin which could not be dissolved in ethanol was confirmed.

In Comparative Example 4, the crystallization operation by means of the poor solvent method was carried out using the ethanol solution of curcumin which was obtained by dissolving curcumin into ethanol by carrying out the stirring operation at 25° C. The average particle diameter of the curcumin microparticles obtained in Comparative Example 4 was about 110 nm, but the width of the particle diameter distribution was widely spread. The particle diameter distributions of the curcumin microparticles obtained in Examples 1 and 2 were in the range of about 90 nm to about 210 nm, while the particle diameter distribution of the curcumin microparticles obtained in Comparative Example 4 was in the range of about 50 nm to about 290 nm; and thus, it was confirmed that the width of the particle diameter distribution of the curcumin microparticles obtained in Comparative Example 4 was more spread than the particle diameter distributions of the curcumin microparticles obtained in Examples 1 and 2. From this result, it is presumed that this is caused by more stable dissolution state of curcumin in ethanol in Examples as compared with Comparative Example 4 due to the difference in the preparation condition of the ethanol solution of curcumin.

Preparation of the Ethanol Solution of γ-Oryzanol

First, the method for preparation of the ethanol solution of γ-oryzanol and the method for retention of the prepared ethanol solution of γ-oryzanol at a prescribed temperature will be explained. Hereinafter, the ethanol solution of γ-oryzanol that is retained at a prescribed temperature is referred to as the ethanol solution of γ-oryzanol after preparation. Meanwhile, the prescribed temperature is the temperature y (° C.) that is obtained by the formula (2).

In Examples, the used γ-oryzanol was γ-oryzanol (Wako special grade) manufactured by Wako Pure Chemical Industries, Ltd., and the used ethanol was ethanol (special reagent grade) manufactured by Wako Pure Chemical Industries, Ltd.

Example 7-1

In Example 7-1, γ-oryzanol and ethanol each were weighed so as to give the ethanol solution of γ-oryzanol with the concentrations of γ-oryzanol and ethanol being respectively 10% by weight and 90% by weight, and then the ethanol solution thus obtained with the total weight of 700 g was taken into a 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm. At this time, the dissolution treatment of γ-oryzanol into ethanol was carried out with the dissolution temperature of 80° C. and with the pressure inside the vessel (pressure inside the attachment) of 0.06 MPaG.

After 30 minutes since the temperature inside the vessel reached 80° C., the rotation number of the rotor was changed to 4500 rpm, and the solution was cooled to 76° C. Then, the ethanol solution of 10% by weight of γ-oryzanol and 90% by weight of ethanol was taken out from the attachment, and it was confirmed with a visual observation that γ-oryzanol was dissolved in ethanol. Then, the prepared ethanol solution of γ-oryzanol was transferred to a glass vessel. When the ethanol solution of γ-oryzanol in the glass vessel was retained in a water bath at 70° C. for 1 hour, it was confirmed with a visual observation that there was no deposit. Temperature of the ethanol solution of γ-oryzanol after being retained in the water bath at 70° C. for 1 hour (ethanol solution of γ-oryzanol after preparation) was 70° C.

Example 7-2

In Example 7-2, γ-oryzanol and ethanol each were weighed so as to give the ethanol solution of γ-oryzanol with the concentrations of γ-oryzanol and ethanol being respectively 5.0% by weight and 95% by weight, and then the ethanol solution thus obtained with the total weight of 700 g was taken into a 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm. At this time, the dissolution treatment of γ-oryzanol into ethanol was carried out with the dissolution temperature of 80° C. and with the pressure inside the vessel (pressure inside the attachment) of 0.06 MPaG.

After 30 minutes since the temperature inside the vessel reached 80° C., the rotation number of the rotor was changed to 4500 rpm, and the solution was cooled to 30° C. Then, the ethanol solution of 5.0% by weight of γ-oryzanol and 95.0% by weight of ethanol was taken out from the attachment, and it was confirmed with a visual observation that γ-oryzanol was dissolved in ethanol. Then, the prepared ethanol solution of γ-oryzanol was transferred to a glass vessel. When the ethanol solution of γ-oryzanol in the glass vessel was retained in a water bath at 30° C. for 1 hour, it was confirmed with a visual observation that there was no deposit. Temperature of the ethanol solution of γ-oryzanol after being retained in the water bath at 30° C. for 1 hour (ethanol solution of γ-oryzanol after preparation) was 30° C.

Example 7-3

In Example 7-3, γ-oryzanol and ethanol each were weighed so as to give the ethanol solution of γ-oryzanol with the concentrations of γ-oryzanol and ethanol being respectively 3% by weight and 97% by weight, and then the ethanol solution thus obtained with the total weight of 700 g was taken into a 1000-cc attachment, which is an airtight vessel. The stirring operation under the heated and pressurized state was carried out by using Clearmix (product name: CLM-2.2S, manufactured by M. Technique Co., Ltd.) with the rotation number of the rotor thereof being 10000 rpm. At this time, the dissolution treatment of γ-oryzanol into ethanol was carried out with the dissolution temperature of 80° C. and with the pressure inside the vessel (pressure inside the attachment) of 0.06 MPaG.

After 30 minutes since the temperature inside the vessel reached 80° C., the rotation number of the rotor was changed to 4500 rpm, and the solution was cooled to 20° C. Then, the ethanol solution of 3% by weight of γ-oryzanol and 97% by weight of ethanol was taken out from the attachment, and it was confirmed with a visual observation that γ-oryzanol was dissolved in ethanol. Then, the prepared ethanol solution of γ-oryzanol was transferred to a glass vessel. When the ethanol solution of γ-oryzanol in the glass vessel was retained in a water bath at 20° C. for 1 hour, it was confirmed with a visual observation that there was no deposit. Temperature of the ethanol solution of γ-oryzanol after being retained in the water bath at 20° C. for 1 hour (ethanol solution of γ-oryzanol after preparation) was 20° C.

As Comparative Example 5, γ-oryzanol and ethanol each were weighed so as to give the ethanol solution of γ-oryzanol with the concentrations of γ-oryzanol and ethanol being respectively 3% by weight and 97% by weight, and then the ethanol solution thus obtained with the total weight of 700 g was taken into the 1000-cc attachment. The dissolution treatment of γ-oryzanol into ethanol was carried out by using Clearmix (product name: CLM-2.2S, manufactured by M. Technique Co., Ltd.) with the rotation number of the rotor thereof being 10000 rpm, the dissolution temperature of 50° C., and the pressure inside the vessel of 0.00 MPaG. After 30 minutes of stirring at 50° C., dissolution of γ-oryzanol was confirmed with a visual observation. When the prepared ethanol solution of γ-oryzanol was cooled to 20° C., deposit was confirmed, so that the subsequent operations were not carried out.

Crystallization Operation by Means of the Poor Solvent Method

Next, in each Example, the γ-oryzanol microparticles were prepared by means of the poor solvent method using the ethanol solution of γ-oryzanol after preparation and the poor solvent described in Table 2. For preparation of the poor solvent, Clearmix (product name: CLM-2.2S, manufactured by M. Technique Co., Ltd.) was used. The stirring was carried out at a room temperature and under a standard pressure (namely, 1 atm=0.101325 MPa) with the rotation number of the rotor thereof being 15000 rpm for 30 minutes. Meanwhile, HPC described in Table 2 is the abbreviation of hydroxypropyl cellulose, one of water-soluble polymers, wherein HPC-SSL manufactured by Nippon Soda Co., Ltd. was used.

The ethanol solution of γ-oryzanol after preparation and the poor solvent after preparation were mixed by using the fluid processing apparatus described in Japanese Patent Laid-Open Publication No. 2011-189348. Meanwhile, the fluid processing apparatus described in Japanese Patent Laid-Open Publication No. 2011-189348 is the one described in FIG. 25 of the said gazette, wherein the opening d20 of the second introduction part is in a concentric circular form surrounding the central opening of the processing surface 2 which is a ring-like disc. Specifically, the poor solvent after preparation was introduced from the first introduction part d1 into between the processing surfaces 1 and 2 at about 0.1 MPaG to about 0.2 MPaG, 450 mL/minute, and 20° C.; and with operating the processing member 10 with the rotation number each described in Table 2, the ethanol solution of γ-oryzanol after preparation was introduced from the second introduction part d2 into between the processing surfaces 1 and 2 at about 0.1 MPaG to about 0.2 MPaG, 150 mL/minute, and at 70° C. in Example 7-1 and at 30° C. in Examples 7-2 to 7-3, thereby the both fluids were mixed in the forced thin film to crystallize the γ-oryzanol microparticles between the processing surfaces 1 and 2. The fluid including the γ-oryzanol microparticles crystallized between the processing surfaces 1 and 2 (hereinafter, this fluid is referred to as the γ-oryzanol microparticles dispersion solution) was ejected from between the processing surfaces 1 and 2 of the fluid processing apparatus. Then, the γ-oryzanol microparticles dispersion solution was recovered in the beaker via the vessel to collect the γ-oryzanol microparticles dispersion solution thus ejected.

The preparation conditions of the ethanol solution of γ-oryzanol, the retention temperature of the ethanol solution of γ-oryzanol, the prescription of the poor solvent, the crystallization conditions of the γ-oryzanol microparticles, and the particle diameter of the obtained γ-oryzanol microparticles are summarized in Table 2.

TABLE 2

| | Ethanol solution of γ-oryzanol | | | | | | | | | Crystallization operation by the poor solvent | | |
|---|---|---|---|---|---|---|---|---|---|---|---|---|
| | Preparation condition | | | | | | Retention condition | | | | | |
| | Concentration of γ-oryzanol [wt %] | Dissolution temperature [° C.] | Pressure inside the vessel [MPaG] | Retention time at the time of Dissolution [min] | Rotation number at the time of Dissolution [rpm] | Dissolution | temperature [° C.] | Deposit; Yes/No | Poor solvent | Rotation number [rpm] | Particle diameter [nm] |
| Example 7-1 | 10 | 80 | 0.06 | 30 | 10000 | ○ | 70 | No | 0.67 wt % HPC/ 99.33 wt % pure water | 1000 | 120 |
| Example 7-2 | 5 | | | | | ○ | 30 | No | | 1000 | 130 |
| Example 7-3 | 3 | | | | | ○ | 20 | No | | 1000 | 100 |
| Comparative Example 5 | 3 | 50 | 0 | 30 | 10000 | ○ | 20 | Yes | — | — | — |

With regard to the item of "Dissolution" described in Table 2, whether or not the γ-oryzanol was dissolved in ethanol was confirmed with a visual observation. When deposit or the γ-oryzanol undissolved in the ethanol solution of γ-oryzanol was confirmed with the visual observation, this was designated with "X", and when γ-oryzanol was not confirmed with the visual observation in the ethanol solution, this was designated as "O".

With regard to whether the deposit was present or not in the ethanol solution of γ-oryzanol in Examples 7-1 to 7-3, after the prepared ethanol solution of γ-oryzanol was retained at the prescribed temperature for 1 hour, confirmation thereof was made with the visual observation; and the result thereof is described in the item of "Deposit; Yes/No" described in Table 2. In Comparative Example 5, as described before, when the prepared ethanol solution of γ-oryzanol was cooled to the prescribed temperature of 20° C., deposit was confirmed.

As the result of the above, at the time when the ethanol solution of γ-oryzanol was prepared by dissolving γ-oryzanol into ethanol, in the case where the stirring operation was carried out under the pressurized state and the temperature condition of 78.3° C. or higher and 130° C. or lower, deposit was not confirmed in the prepared ethanol solution of γ-oryzanol. When the crystallization operation was carried out by means of the poor solvent method using the prepared ethanol solution of γ-oryzanol, the average particle diameter of the obtained γ-oryzanol microparticles was 1 μm or less. In addition, the γ-oryzanol microparticles could be obtained with a narrow width in the particle diameter distribution, in the range of about 80 nm to about 200 nm.

The invention claimed is:

1. A method for producing microparticles, comprising:
preparing a raw material solution having a raw material dissolved in a solvent by carrying out a stirring operation of the raw material and the solvent under a pressurized state and a temperature condition of 78.3° C. or higher and 130° C. or lower to produce a pressurized and heated raw material solution,
wherein the raw material is at least any one of curcumin and γ-oryzanol; and
wherein the solvent is ethanol;
holding a pressurized and heated raw material solution at a temperature which is below a standard boiling point of the ethanol;
carrying out a crystallization operation by means of a poor solvent method using the pressurized and heated raw material solution thereby obtaining microparticles of at least any one of curcumin and γ-oryzanol.

2. The method for producing microparticles according to claim 1,
wherein the raw material is prepared by carrying out the stirring operation of the raw material solution and the solvent under the pressurized state and the temperature condition not causing boiling thereby obtaining a raw material solution wherein solubility of the raw material to the ethanol is increased.

3. The method for producing microparticles according to claim 1,
wherein when the concentration of curcumin in the raw material solution is taken as x (% by weight), the temperature of a raw material solution to be used in the crystallization operation by means of the poor solvent method is a temperature y (° C.) which is indicated by a formula (1) thereby producing curcumin microparticles $$y \geq 0.0222x^3 - 2.7x^2 + 30.511x - 12.833 \qquad (1).$$

4. The method for producing microparticles according to claim 1,
wherein when the concentration of γ-oryzanol in the raw material solution is taken as x (% by weight), the temperature of a raw material solution to be used in the crystallization operation by means of the poor solvent method is a temperature y (° C.) indicated by a formula (2) thereby producing γ-oryzanol microparticles $$y \geq 0.0762x^3 - 0.9429x^2 + 8.8095x + 6 \times 10^{-12} \qquad (2).$$

5. The method for producing microparticles according to claim 1,
wherein the average particle diameter of the microparticles is in a range of 30 nm to 1 μm.

6. The method for producing microparticles according to claim 1,
wherein the raw material is selected from the group consisting of ukon, turmeric, a natural extract from ukon, a natural extract from turmeric, a natural extract from rice bran, a natural extract from a corn oil, a natural extract from grains, and mixtures thereof.

7. The method for producing microparticles according to claim 1,
wherein the amount of the microparticles is increased compared to the amount of microparticles produced using a raw material solution that is not prepared under the pressurized state and the temperature condition.

* * * * *